US00PP27669P3

(12) United States Plant Patent
Danziger

(10) Patent No.: US PP27,669 P3
(45) Date of Patent: Feb. 14, 2017

(54) ***LOBULARIA* PLANT NAMED 'DLOBUBPINK'**

(50) Latin Name: *Lobularia maritima*
Varietal Denomination: DLOBUBPINK

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 96 days.

(21) Appl. No.: 14/544,978

(22) Filed: Mar. 12, 2015

(65) Prior Publication Data

US 2016/0278268 P1 Sep. 22, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Keith Robinson
(74) *Attorney, Agent, or Firm* — Cassandra Bright

(57) ABSTRACT

A new and distinct *Lobularia* cultivar named 'DLOBUBPINK' is disclosed, characterized by long lasting light lavender-pink flowers, semi-trailing and freely branching form, with good vigor and strong structure. The new variety is a *Lobularia*, normally produced as an outdoor garden or container plant.

2 Drawing Sheets

Figure 1:
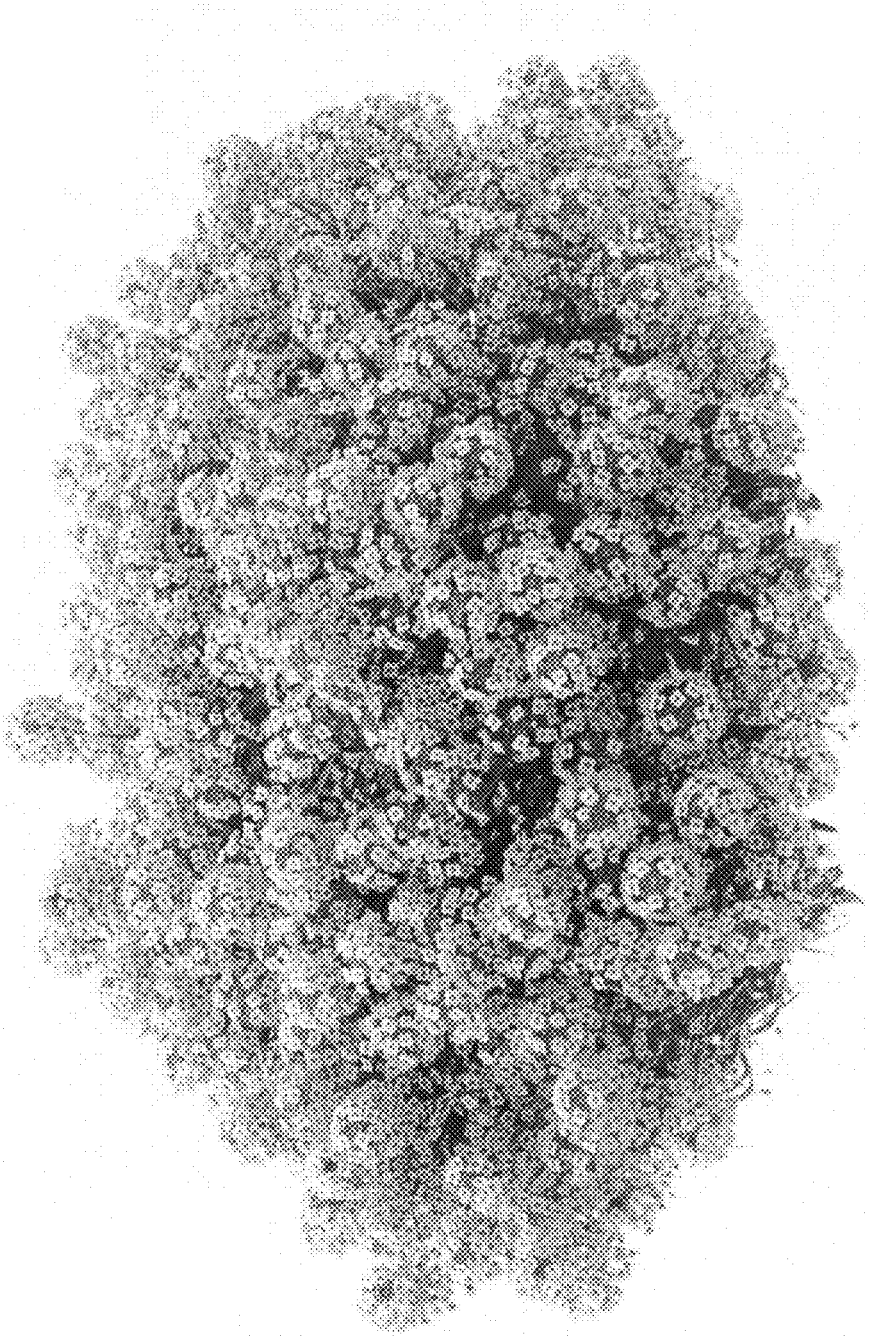

Latin name of the genus and species: *Lobularia maritima.*
Variety denomination: 'DLOBUBPINK'.

BACKGROUND OF THE INVENTION

The new *Lobularia* cultivar is a product of a planned breeding program conducted by the inventor, Gavriel Danziger, in Moshav Mishmar Hashiva, Israel. The objective of the breeding program was to produce new *Lobularia* varieties for ornamental commercial applications. The open pollination resulting in this new variety was made during March of 2012.

The seed parent is the, unpatented, proprietary variety referred to as Lobularia 'AY-12-414'. The pollen parent is unknown as it was an open pollination breeding program. The new variety was discovered in January of 2013 by the inventor in a group of seedlings resulting from the 2012 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in March of 2013 and has shown that the unique features of this cultivar are stable and reproduced true to type in more than 10 successive generations.

SUMMARY OF THE INVENTION

The cultivar 'DLOBUBPINK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBUBPINK' These characteristics in combination distinguish 'DLOBUBPINK' as a new and distinct Lobularia cultivar:

1. Light lavender-pink color.
2. Semi-trailing and vigor plant habit.

3. Freely branching plants with a strong structure.
4. Long flowering period.

Plants of the new cultivar 'DLOBUBPINK' are similar to plants of the seed parent, *Lobularia* 'AY-12-414' in most horticultural characteristics, however, plants of the new cultivar 'DLOBUBPINK' differ in the following;

1. Plants habit is more round, mounded and controlled. The parent habit is loose, open and irregular.
2. More floriferous.
3. Smaller flowers.
4. Flowers are light lavender-pink, while the flowers of the seed parent are lavender.

COMMERCIAL COMPARISON

Plants of the new cultivar 'DLOBUBPINK' are comparable to the patented commercial variety *Lobularia* 'INLBUBLUPR' U.S. Plant Pat. No. 25,516. The two *Lobularia* varieties are similar in most horticultural characteristics; however, the new variety 'DLOBUBPINK' differs in the following:

1. Wider leaves.
2. Flower color—plants of candidate variety has light pink-lilac flowers while flowers of the variety 'INLBUBLUPR' are light violet.
3. Semi trailing and denser form.

Plants of the new cultivar 'DLOBUBPINK' can also be comparable to the unpatented commercial variety *Lobularia* 'Snow Princess'. The two *Lobularia* varieties are similar in most horticultural characteristics; however, the new variety 'DLOBUBPINK' differs in the following:

1. New variety is semi trailing and less vigorous.
2. New variety has smaller leaves.
3. New variety has shorter and tighter inflorescences.
4. New variety is not sterile, whereas plants of 'Snow Princess' are.
5. New variety has smaller flowers

BRIEF DESCRIPTION OF THE PHOTOGRAPHS

The accompanying photograph in FIG. 1 illustrates in full color a typical plant of 'DLOBUBPINK' grown in a greenhouse, in a 13 cm pot. Age of the plant photographed is approximately 7 weeks from sticking.

Figure 2:
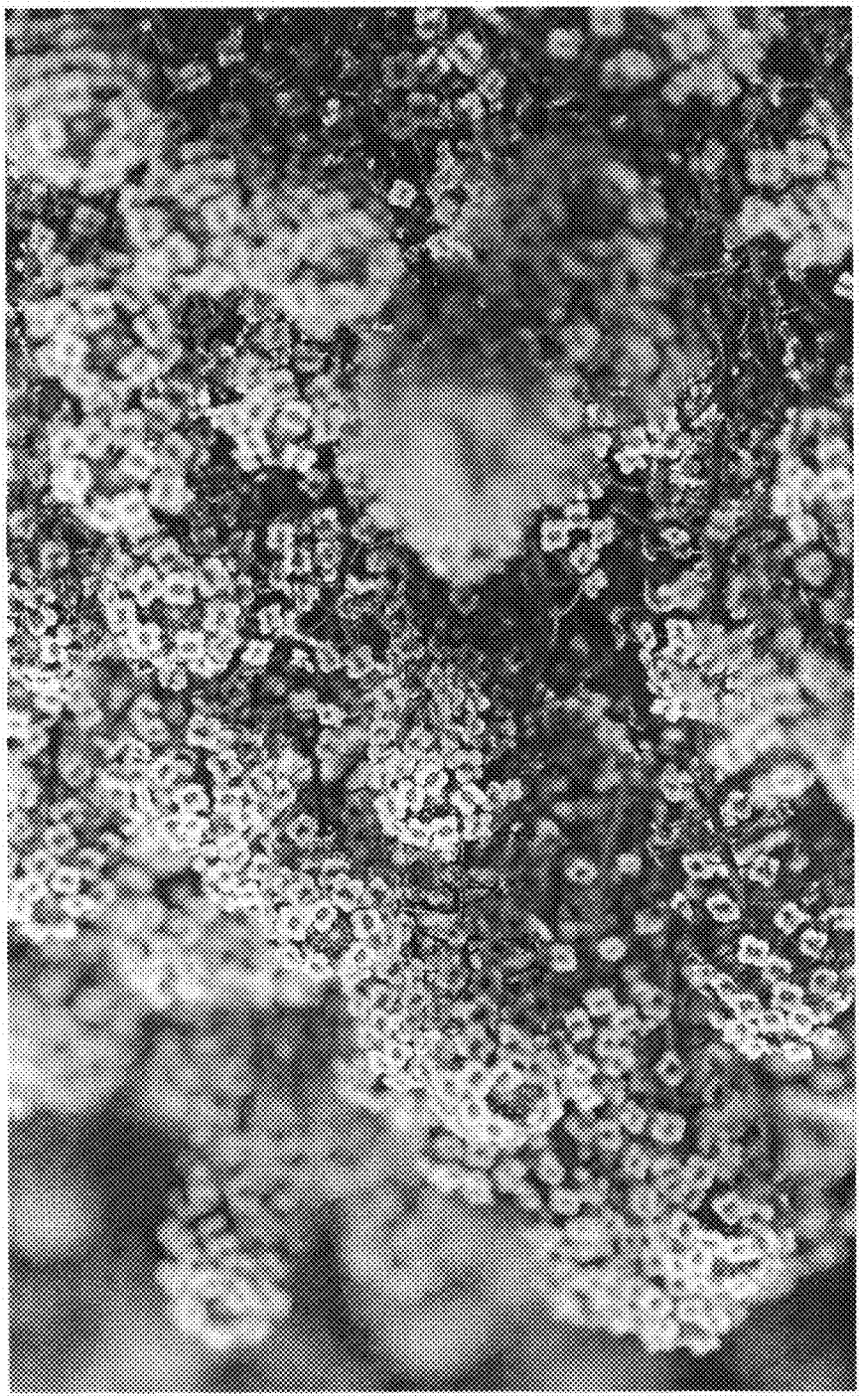

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DLOBUBPINK' plants grown in the Autumn, to Spring in moderate climate in a greenhouse, in Moshav Mishmar Hashiva, Israel. The growing temperature ranged from 20° C. to 30° C. during the day and from 16° C. to 25° C. during the night. General light conditions are high light levels 60,000 to 90,000 Lux Measurements and numerical values represent averages of typical plant types.

Botanical classification: *Lobularia maritima* 'DLOBUBPINK'.

PROPAGATION

Type of propagation typically used: Cutting.

Time to initiate roots: 14-20 days at approximately 16° C.

Root description: Thin, fibrous, freely branching. Near RHS White 155C in color.

Time to produce a rooted young plant: Approximately 4 weeks.

PLANT

Age of plant described: Approximately 7 weeks.

Container size of the plant described: 13 cm.

Growth habit: Semi-trailing and vigorous.

Height: Approximately 18 cm.

Plant spread: Approximately 29 cm (radius).

Growth rate: Vigor, fast growing.

Branching characteristics: Freely Branching.

- *Approximate quantity of lateral branches.*—Approximately 8 primary lateral branches and numerous secondary and tertiary lateral branches.
- *Length of lateral branches.*—Approximately 29 cm.
- *Diameter of lateral branches.*—Approximately 0.25 cm.
- *Texture of lateral branches.*—Slightly Pubescent.
- *Lateral branch shape.*—Hexagonal in cross section.
- *Lateral branch strength.*—Strong (good).
- *Lateral branch color.*—Near RHS Yellow-green 144A.
- *Internode length.*—2-2.5 cm (average).
- *Number of leaves per lateral branch.*—Average 30.

FOLIAGE

Leaf:

- *Arrangement.*—Alternate.
- *Shape of blade.*—Oblanceolate.
- *Average length.*—Approximately 4-5.5 cm. (Mature foliage — 6-7 cm).
- *Average width.*—Approximately 0.8 cm. (Mature foliage — 1.2 cm).
- *Apex.*—Acute.
- *Base.*—Cuncate.
- *Attachment.*—Sessile.
- *Margin.*—Entire.
- *Texture of top surface.*—Glabrous. Slightly Pubescent.
- *Texture of bottom surface.*—Glabrous. Slightly Pubescent.
- *Color.*—Young foliage upper side: Near RHS Green 137B. Young foliage under side: Near RHS Green 137C. Mature foliage upper side: Near RHS Yellow-green 146B. Mature foliage under side: Near RHS Yellow-green 146C.
- *Venation.*—Indistinguishable from foliage blade.
- *Petiole.*—Not present.

FLOWER

Bloom period:

- *Natural season.*—Long lasting flowering period. From March through December in Moshav Mishmar, Israel.
- *In commercial production, flowering begins from a rooted cutting.*—Approximately 4 weeks.

Inflorescence:

- *Arrangement.*—Panicle.
- *Height.*—Approximately 12 cm.
- *Width.*—Approximately 3 cm.
- *Quantity of flowers per inflorescence.*—Approximately 80 flowers.

Bud:

- *Bud shape.*—Globose spherical.
- *Bud length.*—Approximately 1-1.5 mm.
- *Bud diameter.*—Approximately 1 mm.
- *Bud color.*—Near RHS Green 143B.
- *Rate of opening.*—Individual flowers: Fully open approximately 3 days from the bud stage.

Individual flower:

- *Type of individual flowers.*—Single flower.
- *Shape.*—Cross Shaped.
- *Quantity of flowers and buds per plant.*—Approximately 80 flowers and buds per inflorescence — more than 2000 flowers per plant.
- *Diameter of entire flower.*—Approximately 0.7 cm.
- *Depth of flower.*—Approximately less than 1 mm.
- *Flower longevity on plant.*—Approximately 5 days.
- *Persistent or self-cleaning.*—Self-cleaning.
- *Fragrance.*—Sweet, honey like.

Petals:

- *Length of petal.*—Approximately 3 mm.
- *Width of petal.*—Approximately 3.5 mm.
- *Apex.*—Rounded.
- *Base.*—Reniform.
- *Shape of petal.*—Oval.
- *Petal margin.*—Entire.
- *Petal arrangement.*—4 petals fused in a single whorl.
- *Petal number.*—4 petals.
- *Petal appearance.*—Matte.
- *Petal texture.*—Smooth, glabrous, upper and lower surfaces.

Color:

- *Upper surface at first opening.*—Near RHS White N155B.
- *Upper surface at maturity.*—Near RHS Purple 75A.
- *Upper surface at fading.*—Near RHS Purple 75B.
- *Under surface at first opening.*—Near RHS White N155B.
- *Under surface at maturity.*—Near RHS Purple 75A.

*Under surface at fading*.—Near RHS Purple 75B.
*Note*.—Color is darker in cold weather and when grown outside.

Sepal:
*Number*.—4.
*Sepal appearance*.—4 sepals.
*Sepal arrangement*.—4 sepals in a single whorl.
*Sepal length*.—Approximately 1 mm.
*Sepal width*.—Approximately 0.8 mm.
*Sepal shape*.—Elliptic.
*Base*.—Truncate.
*Apex shape*.—Acute.
*Margin*.—Entire.
*Color*.—Near RHS Green 143B.
*Texture*.—Glabrous all surfaces.

Peduncle:
*Length*.—Approximately 2.3-3 cm.
*Diameter*.—Approximately 2 mm.
*Angle*.—Not relevant.
*Strength*.—Strong.
*Color*.—Near RHS Yellow-green 144A.
*Texture*.—Glabrous.

Pedicel:
*Length*.—Approximately 1.2 cm.
*Diameter*.—Approximately 0.5 mm.
*Angle*.—Approximately 80-90 degrees.
*Strength*.—Flexible, moderately strong.
*Color*.—Near RHS Yellow-green 146A.
*Texture*.—Glabrous.

REPRODUCTIVE ORGANS

*Number of pistils per flower*.—1.
*Pistil length*.—Approximately less than 1 mm.
*Stigma shape*.—Rounded to broadly spreading.
*Stigma color*.—Near RHS 143C.
*Style color*.—Near RHS 143C.
*Style length*.—Approximately less than 1 mm.
*Ovary color*.—Near RHS 143C.
*Stamens quantity*.—6.
*Stamen length*.—1.6 mm.
*Filament length*.—About 1.4 mm.
*Filament color*.—Near yellow-Green 145D.
*Anther shape*.—Elliptic.
*Anther size*.—Less than 0.5 mm in length and width.
*Anther color*.—Near RHS Yellow 7B.
*Pollen color*.—Near RHS Yellow 7A.
*Pollen quantity*.—Abundant.

OTHER CHARACTERISTICS

Disease resistance: Neither resistance nor susceptibility to normal diseases of *Lobularia* has been observed. Typical diseases include *Botrytis, Plasmodiophora brassicae* (Alyssum clubroot), *Plasmopara* spp., and various species of *Fusarium, Pythium, Phytophthora*, and *Rhizoctonia*.

Drought tolerance and cold tolerance: Plants of the new *Lobularia* have been noted to have good tolerance at temperatures from 1° C. to 35° C. and also in rain and wind conditions.

Color and shape of fruits and seeds: The fruits and seeds are elliptical and flat, approximately 1.5 mm long and 1.0 mm wide. The color of the mature seed is near RHS Grey-orange 164B. Minute in size, immeasurable.

What is claimed is:

1. A new and distinct cultivar of *Lobularia* plant named 'DLOBUBPINK' as herein illustrated and described.

* * * * *